(12) United States Patent
Yamashita et al.

(10) Patent No.: US 7,758,540 B2
(45) Date of Patent: Jul. 20, 2010

(54) BREAST PUMP

(75) Inventors: Daisuke Yamashita, Tokyo (JP);
Yoshiyuki Oushi, Tokyo (JP)

(73) Assignee: Pigeon Corporation, Tokyo (JP)

( * ) Notice: Subject to any disclaimer, the term of this patent is extended or adjusted under 35 U.S.C. 154(b) by 35 days.

(21) Appl. No.: 12/057,319

(22) Filed: Mar. 27, 2008

(65) Prior Publication Data
US 2008/0243059 A1   Oct. 2, 2008

(30) Foreign Application Priority Data

Mar. 27, 2007   (JP) .............................. 2007-081842

(51) Int. Cl.
*A61M 1/06* (2006.01)
(52) U.S. Cl. ...................................... 604/74
(58) Field of Classification Search .................... 604/74
See application file for complete search history.

(56) References Cited

U.S. PATENT DOCUMENTS

| | | | | |
|---|---|---|---|---|
| 3,822,703 A | * | 7/1974 | Davisson | ..................... 604/75 |
| 4,680,028 A | * | 7/1987 | Stuart | ......................... 604/74 |
| 5,049,126 A | * | 9/1991 | Larsson | ........................ 604/74 |
| 5,749,850 A | | 5/1998 | Williams et al. | |
| 6,749,582 B2 | | 6/2004 | Britto et al. | |
| 7,354,418 B2 | * | 4/2008 | Lee et al. | ....................... 604/74 |
| 2006/0111664 A1 | * | 5/2006 | Samson et al. | ................. 604/74 |
| 2007/0078383 A1 | * | 4/2007 | Tashiro et al. | .................. 604/74 |

FOREIGN PATENT DOCUMENTS

| WO | WO03/013628 | 2/2003 |
|---|---|---|
| WO | WO2004/000390 | 12/2003 |

* cited by examiner

*Primary Examiner*—Nicholas D Lucchesi
*Assistant Examiner*—Diva Ranade
(74) *Attorney, Agent, or Firm*—Kenealy Vaidya LLP

(57) ABSTRACT

A breast pump can include a breast pump main body having a milking portion and negative pressure generating structure for generating negative pressure. The milking portion can include a shape maintaining portion and a negative pressure generating portion that serves as a part of the negative pressure generating structure and can be attached to and detached from an inner side of the shape maintaining portion. At least one end of the negative pressure generating portion on an enlarged diameter side can include a flexible diaphragm portion and a pressing portion formed when a folded-back portion of the diaphragm portion passes an imaginary line of extension of a contact portion contacting the breast to press the breast, while the other end of the negative pressure generating portion is connected to the opening/closing structure.

18 Claims, 5 Drawing Sheets

BREAST PUMP

This application claims the priority benefit under 35 U.S.C. §119 of Japanese Patent Application No. JP2007-81842 filed on Mar. 27, 2007, which is hereby incorporated in its entirety by reference.

BACKGROUND

1. Field

The presently disclosed subject matter relates to a breast pump for expressing milk.

2. Description of the Related Art

Breast pumps having a horn-shaped milking portion with an enlarged diameter that is brought into contact with the breast of a mother, or in other words an enlarged-diameter milking portion, are widely used.

In a well-known constitution for ensuring that the milk, which is formed into a mist by negative pressure generated during milking, does not leak out, a recess is provided in an upper end of a breast pump main body or the like and a deformable member such as a diaphragm is housed in the recess.

More specifically, in a well-known manual breast pump disclosed in U.S. Pat. No. 5,749,850, a handle is connected to the diaphragm, and as a result of the reciprocating motion of the handle, the diaphragm is repeatedly pulled upward, thereby forming negative pressure.

Several other breast pumps having a similar constitution to the breast pump of U.S. Pat. No. 6,749,582 (WO2003/013628, WO2004/000390, and so on) are known.

In the breast pump described in U.S. Pat. No. 5,749,850, a space communicating with a passage that leads from the horn-shaped milking portion is provided in the upper portion of a container for storing liquid, and the volume of this space is varied by the diaphragm.

Hence, the space for forming the negative pressure used for milking is large, and therefore a large volume must be suctioned, leading to deterioration of the suction efficiency.

Further, since the space is formed in a location outside of the horn-shaped milking portion and the diaphragm is attached thereto, a diaphragm attachment structure is used which is complicated and difficult to dismantle. Therefore, it is difficult to clean the breast pump thoroughly, which is inconvenient in terms of hygienic use.

SUMMARY OF THE DISCLOSED SUBJECT MATTER

According to an aspect of the disclosed subject matter, a breast pump can be provided that exhibits superior suction efficiency for forming negative pressure, and in addition to negative pressure functions effectively to achieve a further increase in the milking effect, and is also easy to clean and has a comparative simple constitution.

According to an aspect of the disclosed subject matter, a breast pump can include: a breast pump main body including a milking portion that is brought into contact with a breast of a user to express milk through negative pressure, and negative pressure generating means disposed in the milking portion for generating the negative pressure; storing means that can be attached to and detached from the breast pump main body and are capable of storing the expressed milk; and opening/closing means disposed between the breast pump main body and the storing means for temporarily halting or permitting passage of the milk expressed by the breast pump main body into the storing means. The milking portion comprises: a shape maintaining portion for maintaining the milking portion in an enlarged-diameter horn shape; and a negative pressure generating portion that serves as a part of the negative pressure generating means and can be attached to and detached from an inner side of the shape maintaining portion. At least one end of the negative pressure generating portion on the enlarged diameter side includes a flexible diaphragm portion and a pressing portion formed when a folded-back portion of the diaphragm portion passes an imaginary line of extension of a contact portion contacting the breast to press the breast, while another end of the negative pressure generating portion is connected to the opening/closing means.

According to the above-described aspect of the disclosed subject matter, negative pressure required for milking is formed by the diaphragm portion serving as the negative pressure generating portion, which is a part of the negative pressure generating means that are attached to and detached from the inside of the shape maintaining portion for maintaining the enlarged-diameter horn shape of the milking portion. Hence, the negative pressure formation space is small and the volume to be suctioned is small, and therefore superior suction efficiency is achieved.

Further, the diaphragm-shaped negative pressure generating portion is attached to and detached from the inside of the shape maintaining portion of the milking portion, and therefore detachment and washing can be performed easily.

Moreover, the pressing portion is formed when the folded-back portion of the diaphragm portion serving as the negative pressure generating portion passes an imaginary line of extension of the contact portion contacting the breast to press the breast.

Hence, the pressing portion can be pressed firmly against the periphery of the areola portions of the user's breast in accordance with the timing at which negative pressure is generated by the diaphragm portion as a result of the deformation of the diaphragm portion. Therefore, the breast is not only suctioned but also pressed periodically in synchronization with the suction operation, enabling an extremely efficient milking operation.

Hence, a breast pump that realizes a favorable degree of suction efficiency for forming negative pressure, an further improvement in the milking effect in addition to negative pressure, and a function for periodically pressing the breast in synchronization with the suction operation, and that has a comparatively simple constitution, enabling easy washing, can be provided.

According to a second aspect of the disclosed subject matter, the diaphragm portion of the negative pressure generating portion is connected to a flexible tube body via a support portion, the tube body is connected to the opening/closing means, and the support portion serves as a connection portion connected to driving means that apply a driving force for deforming the diaphragm portion.

According to second aspect of the disclosed subject matter, the diaphragm portion provided in the milking portion is driven to deform and connected to the opening/closing means by the tube body. Therefore, milking can be performed effectively by means of a comparatively simple, compact constitution, and the expressed milk can be led reliably to the container main body.

In accordance with a third aspect of the disclosed subject matter, as the opening/closing means, the tube body is deformed by the deformation movement of the diaphragm portion, thereby displacing in a bending fashion, and thus when the interior of the milking portion is caused to enter a state of negative pressure by the negative pressure generating means, the tube body deforms such that inner walls thereof approach each other and come into contact, and when the state of negative pressure in the interior of the milking portion is released by the negative pressure generating means, the tube body is restored such that the inner walls thereof separate from each other.

According to the third aspect of the disclosed subject matter, the hollow tube body is used as the opening/closing means for temporarily halting or permitting passage of the milk expressed by the breast pump main body into the storing means. Therefore, mechanical strength can be improved by means of a comparatively simple constitution, and handling during washing and so on is easy.

Moreover, the tube body is displaced in a bending fashion so as to open and close the passage in accordance with the negative pressure generation action of the diaphragm portion serving as the negative pressure generating portion, and therefore the negative pressure generation action and opening/closing of the milk passage can be performed in conjunction with each other extremely efficiently.

In a fourth aspect of the disclosed subject matter, the negative pressure generating means comprise the negative pressure generating portion and a manual lever for causing the negative pressure generating portion to perform a negative pressure generating operation.

According to the constitution of the fourth aspect, the negative pressure used for milking can be obtained by the lever, which is operated manually by the hand of the user, and the negative pressure generating means, which generate negative pressure in the milking portion by deforming or displacing upon reception of the lever action.

DETAILED DESCRIPTION OF THE EXEMPLARY EMBODIMENTS

Examples of embodiments of the disclosed subject matter will be described in detail below on the basis of the attached drawings.

Note that the embodiments to be described below are examples of the presently disclosed subject matter, and therefore include various technical features and structures. However, the scope of the disclosed subject matter is not limited to these embodiments.

Figure 1:
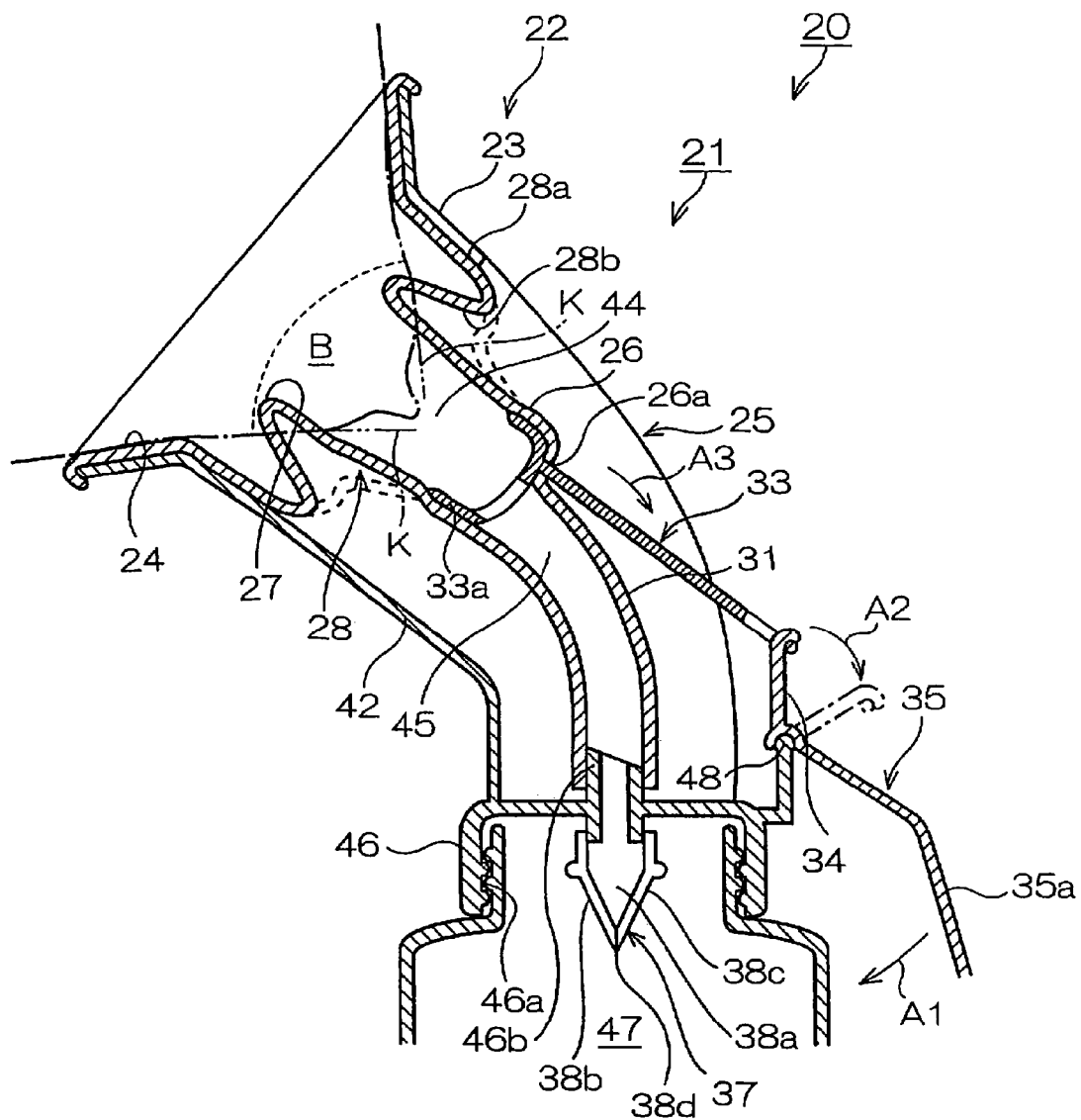
FIG. 1 is a schematic sectional view of an example of a breast pump made in accordance with principles of the disclosed subject matter.
Figure 2:
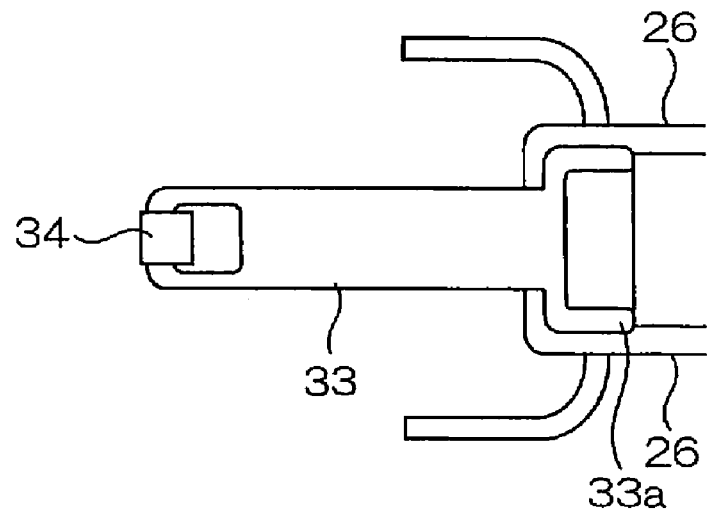
FIG. 2 is a partial plan view of the constitution shown in FIG. 1.

FIGS. 1 and 2 show the constitution of an example of a breast pump made in accordance with principles of the disclosed subject matter. FIG. 1 is a schematic sectional view of the breast pump, and FIG. 2 is a partial plan view of FIG. 1.

FIG. 1 shows parts of the constitution of a breast pump 20. In the drawing, the breast pump 20 can be configured as a container serving as means for storing expressed milk, and includes a breast pump main body 21 that can be attached to and detached from a bottle 47 that can be used as a feeding bottle.

The breast pump main body 21 can include a frame 42 for protecting and supporting a conical or horn-shaped milking portion 22 that opens outward in a diagonally inclined state.

The frame 42 can be molded using a comparatively lightweight, strong synthetic resin material such as polycarbonate, polycycloolefin, polyphenylsulphone, polyethersulphone, polyamide, or polypropylene, for example.

The frame 42 of the breast pump main body 21 comprises an attachment/detachment portion 46 that is attached to and detached from the bottle 47 for storing the expressed milk. The attachment/detachment portion 46 can be a flattened cylindrical part, for example, comprising a female screw portion 46a on its inner side to which a male screw portion formed on the periphery of a bottle mouth of the bottle 47 is screwed. Note that the bottle 47 may be configured such that a pack-shaped bag body can be attached directly or such that a bag body or case body can be attached indirectly via a casing having a male screw portion. Furthermore, instead of attaching/detaching the frame 42 to the bottle 47 directly, when the respective opening diameters of the frame 42 and bottle 47 are different, the bottle 47 may be attached via an adjustment part having both an opening diameter adjustment function and a gripping function, and can be attached using other attachment structures as well.

In FIG. 1, the conical or horn-shaped milking portion 22 that opens outward in a diagonally inclined state is provided in an upper portion of the breast pump main body 21. The milking portion 22 is provided integrally with a tip end side of an open passage that has a slightly enlarged diameter and constitutes an air passage 44 forming a negative pressure space. The milking portion 22 side of the frame 42 comprises a shape maintaining portion 23 having a greatly enlarged diameter in horn shape. The shape maintaining portion 23 is formed integrally with the frame 42 illustrated in FIG. 1, and therefore the shape maintaining portion 23 can be formed from a similar synthetic resin material or the like as compared with the frame 42. Thus, the shape maintaining portion 23 has a comparatively high degree of rigidity and is unlikely to deform. Note that the frame 42 and shape maintaining portion 23 may be provided as separate, attachable bodies instead of being formed integrally.

Further, a horn-shaped contact portion 24 having a substantially identical shape to the shape maintaining portion 23 is provided on the inside of the shape maintaining portion 23. For example, the contact portion 24 is attached detachably such that the tip end of the contact portion 24 curves around the entire outer periphery on the tip end of the shape maintaining portion 23 from the inside to the outside, as shown in the drawing.

More specifically, for example, the contact portion 24 is attached to and detached from the inside of the shape maintaining portion 23 by providing the contact portion 24 and the shape maintaining portion 23 with respective latching structures or means (for example, a latch projection portion and a latch recess portion, dimensions that allow pressure-insertion, and so on). The contact portion 24 is formed from a comparatively flexible elastic body (elastomer) such as silicone rubber, natural rubber, etc., to ensure that it can contact the surface of a breast B, indicated by a dot-dash line, without applying uncomfortable contact thereto.

The contact portion 24 is a flexible, horn-shaped tubular body, but when attached to the shape maintaining portion 23, it can conform with and contacts the shape maintaining portion 23, and therefore remains fitted to the breast B without deforming upon insertion of the breast B. Note that FIG. 1 shows an imaginary line of extension K of the inner surface (the surface that touches the breast B) of the contact portion 24.

Meanwhile, a negative pressure generating portion 28 serving as negative pressure generating means extending in a direction heading toward the bottle 47 and provided integrally with the contact portion 24 in FIG. 1 can be made of the same material as the contact portion 24 and can extend in tubular form. The negative pressure generating portion 28 is formed so as not to come into contact with the shape maintaining portion 23, and is can be formed with a thinner material thickness than the contact portion 24 so as to deform easily.

In other words, the negative pressure generating portion 28 serves as a diaphragm portion that deforms actively when manipulated by a user in a manner to be described below between the state shown by a solid line and the state shown by a broken line in FIG. 1.

More specifically, in the state shown by the solid line, which is the state at the start of use, a deforming wall 28b is folded back toward the inside of a tubular outer peripheral wall 28a. In the state shown by the broken line, which occurs when the negative pressure generating portion 28 is deformed, the deforming wall 28b moves in a direction away from the milking portion 22, enabling the generation of negative pressure. When the manipulation is subsequently relaxed, the deforming wall 28b is restored from the deformed state such that the negative pressure is released, and returns to the pre-use state shown by the solid line.

Note that the contact portion 24 and negative pressure generating portion 28 need not be formed integrally, and instead, the contact portion 24 and negative pressure generating portion 28 may be formed as separate bodies disposed with a boundary position therebetween, which can be attached to and detached from each other tightly.

When the deforming wall 28b of the negative pressure generating portion 28, which serves as a diaphragm portion, deforms upon release of the negative pressure, an apex of the folded back part that is folded back inwardly, as a pressing portion 27, passes the aforementioned imaginary line of extension K of the contact portion 24 and projects onto the breast B side so as to press a portion of the areolae of the breast, not shown in the drawing, inward.

Thus, once the negative pressure has risen, the breast is pressed firmly such that a suitable degree of stimulation for milking is applied about the area of the areolae, and as a result, the milking effect is enhanced even further.

Further, one end of the negative pressure generating portion 28, or in other words the vicinity of the upper end in FIG. 1, is formed integrally with the contact portion 24, but the other end portion, i.e. the lower end side, is formed with a support portion 26 so that a shape maintaining portion 33a on the end portion of an arm portion 33 to be described below can be accommodated detachably.

The inside of the support portion 26 forms a negative pressure space 44 serving as a passage for the expressed milk.

A hollow tube body 31 extends from the support portion 26 toward the lower part of FIG. 1. A lower end of the tube body 31 is attached to a hollow tubular attachment portion 46b that stands upright from the attachment/detachment portion 46 of the frame 42 and serves as a lid of the bottle 47.

The tube body 31 connects the negative pressure space 44 provided in series with the milking portion 22 to the interior of the bottle 47 by means of a hollow space 45 provided therein.

If the functions described above are provided or desired, the tube body 31 need not be integrated with the diaphragm portion 28 and support portion 26, and instead may be provided separately. In this embodiment, however, these components are formed integrally.

As will be described below, the tube body 31 is formed from a bendable material that is flexible enough to be deformed or bent easily during a negative pressure forming operation but has sufficient strength not to break when bent repeatedly. Further, the tube body 31 may take an elliptical tubular shape or an oval tubular shape rather than a cylindrical shape.

A small valve chamber 37 serving as opening/closing means is connected to the lower end of the tube body 31.

More specifically, the small valve chamber 37 can take the form of a hollow cap formed entirely from an elastic body (elastomer) such as silicone rubber or natural rubber, etc., and has a space 38a in its interior. Two side walls 38b, 38c on a lower end side of the small valve chamber 37 are formed thinly, and together constitute a valve body made of elastic inclined walls that approach each other gradually toward the lower end, thereby reducing the width of the valve body. A slit 38d is provided in the lower end where the two side walls 38b, 38c approach each other, and when the expressed milk accumulates to a predetermined amount in the space 38a of the small valve chamber 37, the slit 38d opens under the weight of the milk and in accordance with pressure variation occurring when negative pressure is released, as will be described below, whereby the milk drips into the bottle 47. Further, by forming the slit 38d in the lower end of the inclined walls, air in the bottle 47 can be prevented from entering the space 38a in the interior of the small valve chamber 37 during periods of negative pressure.

Further, as shown in FIG. 1, in the breast pump 20, the negative pressure generating portion 28 is driven by a manual lever (to be referred to as the "lever" hereafter) 35 that can be operated manually, for example.

A constitutional example of these driving means will now be described.

As shown in FIG. 1, an upper end of the lever 35 in a gripping region 35a thereof is fixed rotatably and detachably to a spindle portion 48 that stands upright from the attachment/detachment portion 46 of the frame 42. A part of the lever 35 forms a short rod-shaped or plate-shaped link 34 that extends upward from the periphery of the spindle portion 48. A tip end of the link 34 is fixed rotatably and detachably about a spindle on a lower end of the arm portion 33, which is connected to the negative pressure generating portion 28.

More specifically, the arm 33 is formed from a material possessing rigidity, and as shown in FIGS. 1 and 2, the shape maintaining portion 33a on the milking portion 22 side of the arm portion 33 is formed in a cup shape having an enlarged diameter. The shape maintaining portion 33a can be mounted in the interior of the support portion 26 by penetrating the arm portion 33 from the milking portion 22 side into a support portion opening 26a. Thus, the shape maintaining portion 33a functions to prevent the support portion 26 from deforming under the negative pressure. Note that the arm portion 33 may be formed integrally with the support portion 26 and so on by being integrally molded thereto using insert molding or the like. From this position, the arm portion 33 extends diagonally downward, and as shown by the enlargement in FIG. 2, is engaged to the aforementioned link 34 so as to be capable of rotating about the lower end thereof.

This exemplary embodiment is constituted in the manner described above, and next, an operation of the breast pump 20 will be described.

As shown in FIG. 1, when the lower end side of the lever 35 is caused to approach the bottle 47 manually and rotated about the spindle portion 48 in the manner shown by arrow A1, the link 34 rotates about the spindle portion 48 in the manner shown by arrow A2.

Hence, the arm portion 33 moves in the manner shown by arrow A3 so as to be pulled by the shape maintaining portion 33a mounted in the interior of the support portion 26. As a result, the diaphragm portion 28 serving as the negative pressure generating portion is stretched so as to deform into the shape shown by the dotted lines. Thus, the negative pressure in the negative pressure space 44 (the contact portion 24 side of which is blocked by the breast B) increases such that milk is expressed from the breast B, and the expressed milk enters the negative pressure space 44.

In synchronization with the movement described above, the support portion 26 of the negative pressure generating means 25 displaces downward in FIG. 1, but since the tube body 31 is capable of deformation, it can follow this movement sufficiently.

Next, when the user loosens her grip, the restoration force of the deforming wall 28b acts such that the lever 35 moves in an opposite direction to the arrow A1 in FIG. 1 and the link 34 moves in an opposite direction to the arrow A2 to return to the solid line position. Also, the arm portion 33 moves upward in an opposite direction to the arrow A3, and therefore the diaphragm portion 28 returns to the solid line state.

Hence, in the deforming wall 28b of the negative pressure generating portion 28, i.e. the diaphragm portion, a pressing portion 27, which is formed at the apex of the folded-back part that is folded back toward the inside when the deforming wall 28b deforms during release of the negative pressure, passes the imaginary line of extension K of the contact portion 24 so as to project onto the breast B side, and is pressed to the periphery of the areolae, not shown in the drawing. Therefore, once the negative pressure has risen, the breast is pressed firmly such that a suitable degree of stimulation for milking is applied about the area of the areolae, and as a result, milking is encouraged.

When the negative pressure space 44 returns to its original atmospheric pressure state (or when negative pressure is released), the milk that has accumulated in the negative pressure space 44 following milking passes through the tube body 31 communicating with the space 44 and is led into the space 38a of the small valve chamber 37 serving as the opening/closing means. Once the milk has accumulated in the space 38a to a predetermined amount, the slit 38d opens under the weight of the milk and in accordance with pressure variation occurring when the negative pressure is released, as will be described below, whereby the milk drips into and accumulates in the bottle 47.

Hence, when the user repeatedly performs an operation in which the lever 35 is gripped and moved in the direction of the arrow A1 and then the grip is loosened and the lever 35 reverses its movement, negative pressure formation in the negative pressure space 44 by the diaphragm portion 28 and release of the negative pressure are performed alternately, as a result of which a required amount of milk can be stored in the bottle 47.

According to the breast pump 20 of this embodiment, a breast pump that realizes a favorable degree of suction efficiency for forming negative pressure, a further improvement in the milking effect in addition to negative pressure, and a function for periodically pressing the breast in synchronization with the suction operation, and a breast pump that has a comparatively simple constitution, enabling easy washing, can be provided.

Figure 3:
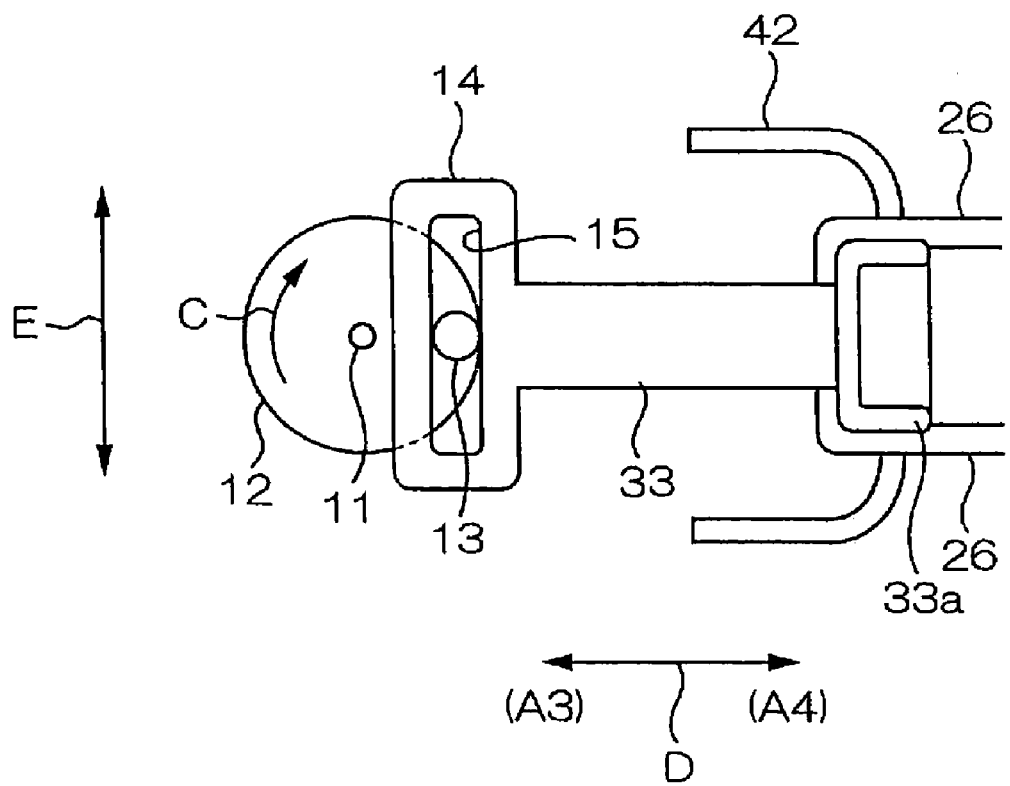
FIG. 3 is a partial plan view showing parts of a modified example of the breast pump shown in FIG. 1.

FIG. 3 is a schematic plan view of a modified example of the first embodiment, and shows a simplification of certain parts of a constitutional example in which the diaphragm portion 28 serving as the negative pressure generating portion is driven via the arm portion 33.

An attachment portion 14 is provided on the tip end of the arm portion 33, and an elongated hole 15 extending in an orthogonal direction to the extension direction of the arm portion 33 is formed in the attachment portion 14. A pin 13 provided near the outer periphery and forms an eccentric cam 12, the pin 13 is inserted into the elongated hole 15.

A rotary shaft of an electric motor or the like, for example, can be fixed to a drive shaft 11 in the center of the eccentric cam 12.

This modified example is constituted as described above such that when the drive shaft 11 rotates, causing the eccentric cam 12 to rotate in the direction of arrow C, the pin 13 of the eccentric cam 12 reciprocates within the elongated hole 15 in the direction of an arrow E, and accordingly, the arm portion 33 reciprocates in the direction of arrow D. This movement corresponds to reciprocation in the direction of arrow A3 and an opposite direction thereto (A4 direction), as shown in FIG. 1.

Hence, the negative pressure generating means 25 may be driven through mechanical driving apparatus such as an electric driving motor instead of being operated manually.

Next, a second embodiment will be described.

Figure 4:
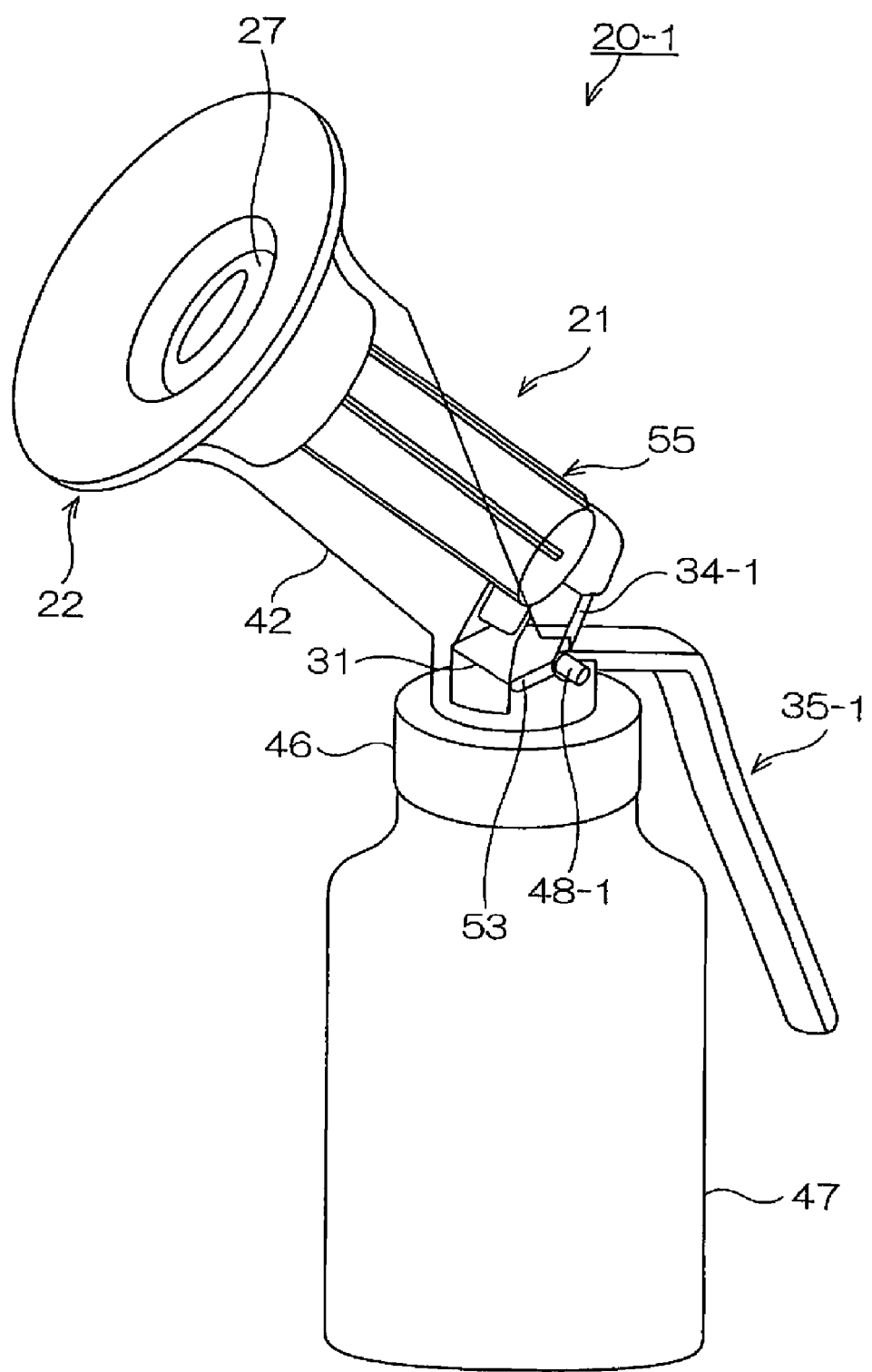
FIG. 4 is a schematic perspective view of a second example of a breast pump made in accordance with principles of the disclosed subject matter.
Figure 5:
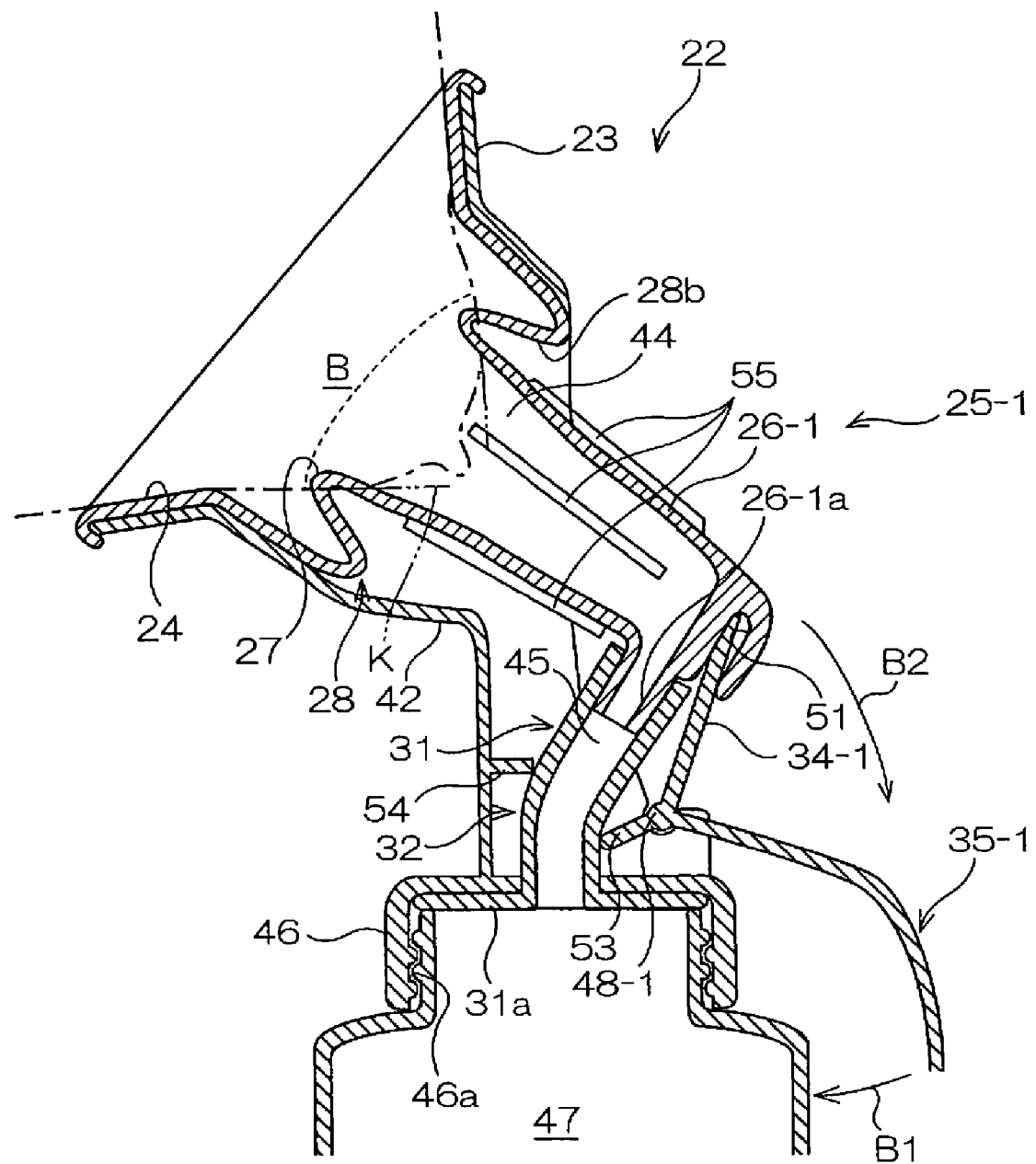
FIG. 5 is a sectional view showing parts of the breast pump of FIG. 4 in an unused state.
Figure 6:
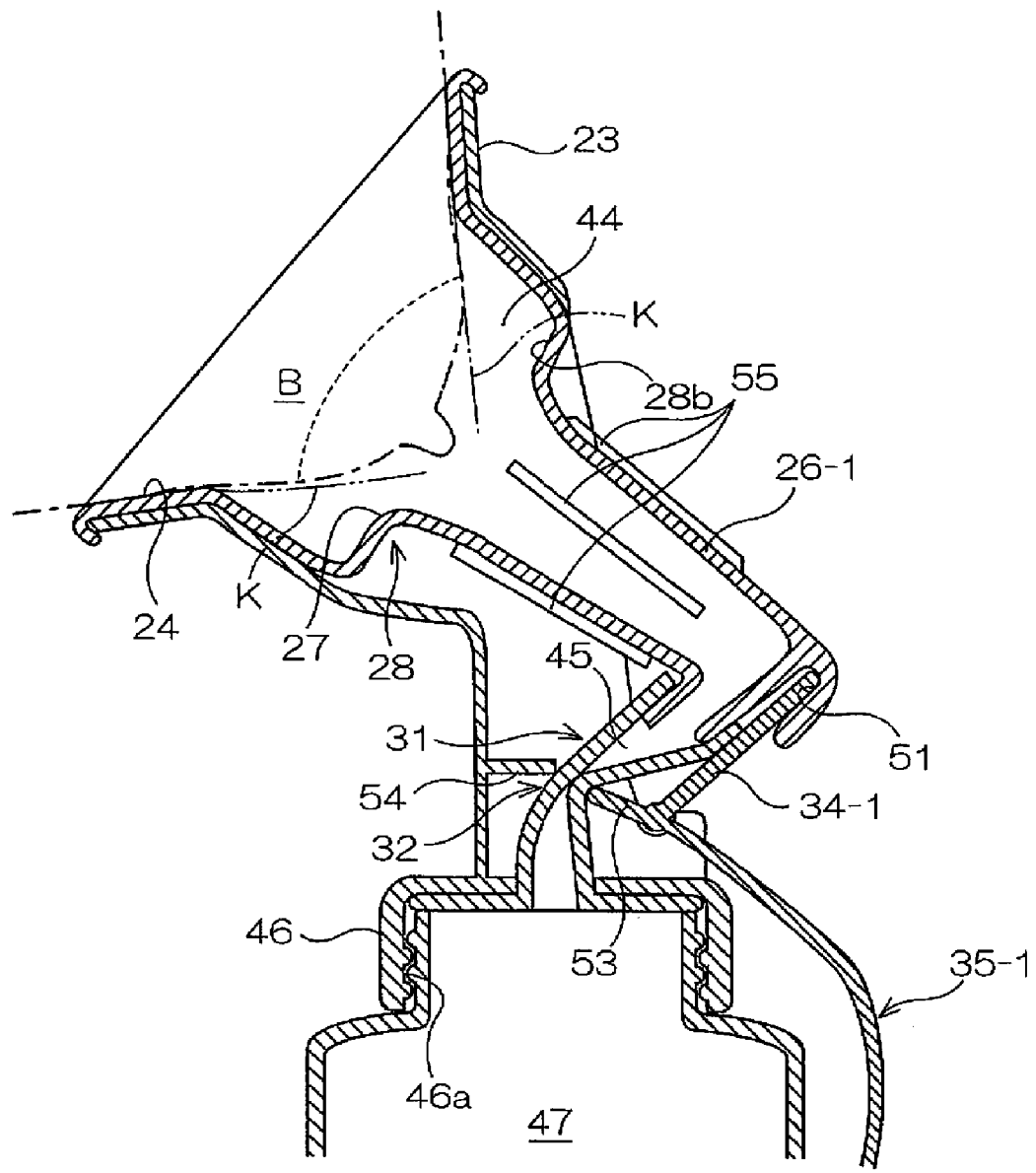
FIG. 6 is a sectional view showing parts of the breast pump of FIG. 4 during movement.

FIGS. 4 to 6 are schematic sectional views showing parts of a breast pump according to the second embodiment.

In FIGS. 4 to 6, locations or structures having identical reference symbols as compared to those used in FIGS. 1 and 2 illustrating the first embodiment can share similar or identical constitutions, and therefore duplicate description thereof has been omitted.

Negative pressure generating means 25-1 of the milking portion 22 of a breast pump 20-1 differ slightly from the first embodiment in the constitution of a support portion 26-1, which is formed as a continuation of the diaphragm portion 28 serving as the negative pressure generating means. More specifically, as shown in the drawings, the support portion 26-1 is slightly longer, and the arm portion 33 and shape maintaining portion 33a are therefore not formed. Further, a pocket-shaped or slit-shaped housing portion 51 is formed in a terminal end portion of the support portion 26-1, and a long link 34-1 taking the shape of a plate that extends upward from the lever 35 is inserted into an opening of the housing portion 51.

While the support portion 26-1 is increased in length, a set of reinforcement ribs 55 for maintaining the shape of the support portion 26-1 during periods of negative pressure can be used in place of the shape maintaining portion 33a and can be formed in four locations so as to project from the outer periphery of the cylindrical support portion 26-1. Note that the reinforcement ribs 55 may be molded integrally with and/or into the negative pressure generating portion 28 using a rigid material or by varying the thickness of the support portion 26-1 instead of being formed.

In this embodiment, when the negative pressure generating portion 28 generates negative pressure in the negative pressure space 44, the tube body 31 functions to block the negative pressure space 44 and a passage 45 communicating with the bottle 47 at a midway point on the passage 45, and therefore serves as an opening/closing structure or means for opening and closing the passage between the space 44 and the bottle 47.

Hence, in the second embodiment, a small valve chamber serving as the opening/closing structure or means in the first embodiment is not necessary and therefore not formed.

Further, a short boss-shaped portion 53 forming a part of deformation promoting structure or means and extending from a spindle portion 48-1 toward the tube body 31 can be formed integrally with the lever 35-1. The boss-shaped portion 53 is positioned to correspond to a bend portion 32 of the tube body 31, and a projecting portion 54 is provided as another part of the deformation promoting structure or means so as to project from an inner wall of the frame 42 in a position likewise corresponding to the bend portion 32. Note that the spindle portion 48-1 is constituted by forming a notch portion in the wall surface of the frame 42 and engaging a shaft portion projecting outward from the lever 35-1 with the notch portion.

Further, the tube body 31 can be formed separately from the support portion 26-1, and can be configured to communicate with the bottle 47 on a lower end side by means of a seat plate portion 31a, which is sandwiched fixedly between the bottle 47 and the attachment/detachment portion 46. The tube body 31 can also be configured to communicate with the negative pressure space 44 on an upper end side by means of an attachment/detachment projecting portion 26-1a projecting outward from a lower end of the support portion 26-1, which is inserted into the tube body 31.

This embodiment is constituted as described above such that when the lever 35-1 is moved in the direction of arrow B1 from the state shown in FIG. 5, a terminal end portion of the support portion 26-1 is moved in the direction of arrow B2 by the link 34-1. As shown in FIG. 6, the deforming wall 28b of the diaphragm portion 28 deforms toward the bottle 47 side such that negative pressure is formed in the negative pressure space 44.

Simultaneously, as shown in FIG. 6, the boss-shaped portion 53 comes into contact with the lever 35-1 side outer surface of the tube body 31 while on the opposite surface thereto, the projecting portion 54 abuts against the outer surface of the tube body 31. As a result, the tube body 31 is pressed between the boss-shaped portion 53 and projecting portion 54, and is therefore encouraged to bend reliably so as to become tightly closed.

As a result of this rapid bending, the inner surfaces of the tube body 31 approach each other and then come into contact, whereby a closed hollow space is formed. By bending the tube boy 31 quickly and reliably in this manner, the negative pressure in the negative pressure space 44 is cut off from the bottle 47 side, and therefore milking is performed appropriately without leakage such that the milk accumulates above the bent location 32 of the tube body 31.

Next, when the user loosens her grip, the restoration force of the deforming wall 28b acts such that the lever 35-1 moves in an opposite direction to the arrow B1 in FIG. 5 and the link 34-1 moves in an opposite direction as compared to arrow B2. As a result, the diaphragm portion 28 returns to the state shown in FIG. 5.

Hence, the space indicated by the reference numeral 44 returns to its original atmospheric pressure state (or negative pressure release state), and at the same time, the bend portion 32 of the tube body 31 extends so as to return to the state shown in FIG. 5, whereby the blockage of the hollow passage is released. As a result, the passage between the space 44 and the bottle 47 is opened, and the milk that has accumulated in the space 44 following milking drips into the bottle 47.

Since the small valve chamber is not provided, the passage between the space 44 and the bottle 47 can be opened and closed by means of a simple constitution.

Other actions can be identical or similar to those of the first embodiment.

Incidentally, the presently disclosed subject matter is not limited to the embodiments described above.

For example, as long as a constitution for opening and closing the tube body is provided, the breast pump need not be driven manually, and may be a so-called electric breast pump in which a diaphragm is driven electrically, as in the modified example described above, to switch between negative pressure and atmospheric pressure intermittently, and the corresponding driving means may be formed separately from the breast pump main body as mounted driving means or connected thereto using another tube. Note that the various constitutions of the embodiments may be substituted for one another, and individual constitutions of the embodiments and the modified examples may be omitted or combined with another constitution not described above if necessary or desired for a particular application.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents. All related art references described above are hereby incorporated in their entirety by reference.

What is claimed is:

1. A breast pump comprising:
a breast pump main body including a milking portion configured to be brought into contact with a breast of a user to express milk via negative pressure, and means for generating negative pressure disposed in said milking portion for generating said negative pressure;
means for storing said expressed milk configured to be attached to and detached from said breast pump main body; and
means for opening/closing and temporarily halting and permitting passage of said milk expressed by said breast pump main body into said means for storing, said means for opening/closing disposed between said breast pump main body and said means for storing,
wherein said milking portion includes:
a shape maintaining portion configured to maintain said milking portion in an enlarged-diameter horn shape; and
a negative pressure generating portion that serves as a part of said means for generating negative pressure configured to be attached to and detached from an inner side of said shape maintaining portion, and
at least one end of said negative pressure generating portion at an enlarged diameter side includes a pressing portion, the pressing portion includes an apex of a folded-back portion of said negative pressure generating portion, while another end of said negative pressure generating portion is connected to said means for opening/closing.

2. The breast pump according to claim 1, wherein said negative pressure generating portion is a diaphragm portion connected to a flexible tube body via a support portion, said tube body is connected to said means for opening/closing, and said support portion serves as a connection portion connected to means for applying a driving force for deforming said diaphragm portion.

3. The breast pump according to claim 2, wherein said means for generating negative pressure include said negative pressure generating portion and a manual lever configured to cause said negative pressure generating portion to perform a negative pressure generating operation.

4. The breast pump according to claim 1, wherein said means for opening/closing is a tube body, the tube body includes means for deforming said tube body by a deformation movement of said diaphragm portion, thereby displacing said tube body in a bending fashion, and thus when an interior of said milking portion is caused to enter a state of negative pressure by said means for generating negative pressure, said tube body deforms such that inner walls of the tube body approach each other and come into contact with each other, and when said state of negative pressure in the interior of said milking portion is released by said means for generating negative pressure, said tube body is restored such that said inner walls of the tube body separate from each other.

5. The breast pump according to claim 4, wherein said means for generating negative pressure include said negative pressure generating portion and a manual lever configured to cause said negative pressure generating portion to perform a negative pressure generating operation.

6. The breast pump according to claim 5, wherein said means for opening/closing includes a boss shaped portion extending from a said manual lever, the boss shaped portion configured to contact the tube body and cause the tube body to deform such that the inner walls of the tube body approach each other and come into contact with each other.

7. The breast pump according to claim 6, wherein said means for opening/closing includes a projecting portion extending from a frame portion and located opposite the boss shaped portion such that the tube body is squeezed between the projecting portion and the boss shaped portion when said means for generating negative pressure is operated.

8. The breast pump according to claim 1, wherein said means for opening/closing includes a valve chamber.

9. A breast pump comprising:
   a breast pump main body including a milking portion configured to be brought into contact with a breast of a user to express milk via negative pressure, and a negative pressure generating structure disposed adjacent said milking portion and configured to generate negative pressure in the milking portion;
   a storing enclosure configured to be attached to and detached from said breast pump main body and capable of storing said expressed milk; and
   an opening/closing structure disposed between said breast pump main body and said storing enclosure and configured to selectively permit passage of said milk expressed by said breast pump main body into said storing enclosure,
   wherein said milking portion includes:
      a shape maintaining portion configured to maintain said milking portion in an enlarged-diameter horn shape; and
      a negative pressure generating portion that serves as a part of said negative pressure generating structure, the negative pressure generating portion configured to be attached to and detached from an inner side of said shape maintaining portion, and
      at least one end of said negative pressure generating portion at an enlarged diameter side includes a pressing portion, the pressing portion includes an apex of a folded-back portion of said negative pressure generating portion.

10. The breast pump according to claim 9, wherein said negative pressure generating portion is a diaphragm portion connected to a flexible tube body via a support portion, said tube body is connected to said opening/closing structure, and said support portion serves as a connection portion connected to a drive device.

11. The breast pump according to claim 9, wherein said opening/closing structure is configured such that said a tube body is deformed by a deformation movement of said diaphragm portion, thereby displacing said tube body in a bending fashion, and thus when an interior of said milking portion is caused to enter a state of negative pressure by said negative pressure generating structure, said tube body deforms such that inner walls of the tube body approach each other and come into contact with each other, and when said state of negative pressure in the interior of said milking portion is released by said negative pressure generating structure, said tube body is restored such that said inner walls of the tube body separate from each other.

12. The breast pump according to claim 9, wherein said negative pressure generating structure includes said negative pressure generating portion and a manual lever configured to cause said negative pressure generating portion to perform a negative pressure generating operation.

13. A breast pump, comprising:
   a frame structure that includes a cup portion configured to correspond in shape to a human breast;
   a flexible diaphragm located within the frame structure;
   an arm structure connected to the flexible diaphragm and moveable with respect to the frame structure;
   a storage device located adjacent the frame structure and flexible diaphragm; and
   a valve structure located between the flexible diaphragm and the storage device, wherein
   the flexible diaphragm includes a portion that extends substantially parallel with the frame structure and a portion that is substantially Z-shaped in cross section such that the diaphragm extends substantially parallel with and out of the frame structure for a first certain length and then the flexible diaphragm extends outward and back into the frame structure for a second certain length and then outward and again substantially parallel with and towards the cup shaped portion of the frame structure for a third certain length.

14. The breast pump according to claim 9, wherein said valve structure includes a valve chamber.

15. The breast pump according to claim 13, further comprising reinforcement ribs located on the first certain length of the diaphragm.

16. The breast pump according to claim 13, wherein said arm structure is attached to a lever and is configured to move the first certain length of the flexible diaphragm with respect to the third certain length of the flexible diaphragm to induce a negative pressure within the flexible diaphragm.

17. The breast pump according to claim 12, wherein said opening/closing structure includes a boss shaped portion extending from said manual lever the boss shared portion configured to contact the tube body and cause the tube body to deform such that the inner walls of the tube body approach each other and come into contact with each other.

18. The breast pump according to claim 17, wherein said opening/closing structure includes a projecting portion extending from a frame portion and located opposite the boss shaped portion such that the tube body is squeezed between the projecting portion and the boss shaped portion when said negative pressure generating structure is operated.

* * * * *